(12) United States Patent
Schmidt et al.

(10) Patent No.: US 10,144,685 B2
(45) Date of Patent: *Dec. 4, 2018

(54) REMOVAL OF AROMATIC IMPURITIES FROM AN ALKENE STREAM USING AN ACID CATALYST

(71) Applicant: Saudi Basic Industries Corporation, Riyadh (SA)

(72) Inventors: Roland Schmidt, Wiehl (DE); Shahid Azam, Riyadh (SA)

(73) Assignee: SAUDI BASIC INDUSTRIES CORPORATION, Riyadh (SA)

(*) Notice: Subject to any disclaimer, the term of this patent is extended or adjusted under 35 U.S.C. 154(b) by 0 days.

This patent is subject to a terminal disclaimer.

(21) Appl. No.: 15/116,858

(22) PCT Filed: Feb. 5, 2015

(86) PCT No.: PCT/IB2015/050860
§ 371 (c)(1),
(2) Date: Aug. 5, 2016

(87) PCT Pub. No.: WO2015/118469
PCT Pub. Date: Aug. 13, 2015

(65) Prior Publication Data
US 2017/0174586 A1     Jun. 22, 2017

Related U.S. Application Data

(60) Provisional application No. 61/937,095, filed on Feb. 7, 2014.

(51) Int. Cl.
*C07C 7/17* (2006.01)
*C10G 29/20* (2006.01)
*C10G 50/00* (2006.01)
*C10G 17/02* (2006.01)
*C10G 17/095* (2006.01)
*C07C 7/148* (2006.01)
*C08F 210/14* (2006.01)
*C07C 7/171* (2006.01)

(52) U.S. Cl.
CPC .......... *C07C 7/171* (2013.01); *C07C 7/14858* (2013.01); *C07C 7/14875* (2013.01); *C08F 210/14* (2013.01); *C10G 17/02* (2013.01); *C10G 17/095* (2013.01); *C10G 29/205* (2013.01); *C10G 50/00* (2013.01); *C10G 2300/1088* (2013.01); *C10G 2300/201* (2013.01)

(58) Field of Classification Search
CPC . C07C 7/171; C07C 7/14858; C07C 7/14875; C07C 7/17; C07C 11/08; C07C 11/10; C07C 11/107; C08F 210/14
USPC .................. 585/519, 831; 526/77
See application file for complete search history.

(56) References Cited

U.S. PATENT DOCUMENTS

| | | |
|---|---|---|
| 2,860,173 A | 11/1958 | Jones |
| 3,094,568 A | 6/1963 | Hay |
| 3,129,256 A | 4/1964 | Hay et al. |
| 3,131,230 A | 4/1964 | Hervert |
| 3,631,120 A | 12/1971 | Eberly, Jr. |
| 4,016,218 A | 4/1977 | Haag et al. |
| 4,094,922 A | 6/1978 | Bartek et al. |
| 4,209,383 A | 6/1980 | Herout et al. |
| 4,243,828 A | 1/1981 | Kerr et al. |
| 4,764,440 A | 8/1988 | Jones et al. |
| 5,030,785 A | 7/1991 | Huss, Jr. et al. |
| 5,107,048 A | 4/1992 | Huss, Jr. et al. |
| 5,149,894 A | 9/1992 | Holtermann et al. |
| 5,171,915 A | 12/1992 | Forbus et al. |
| 5,210,350 A | 5/1993 | Solofo et al. |
| 5,491,208 A | 2/1996 | Tanaglia et al. |
| 5,648,579 A | 7/1997 | Kulprathipanja et al. |
| 5,731,101 A | 3/1998 | Sherif et al. |
| 5,750,455 A | 5/1998 | Chauvin et al. |
| 5,824,832 A | 10/1998 | Sherif et al. |
| 5,863,419 A | 1/1999 | Huff, Jr. et al. |

(Continued)

FOREIGN PATENT DOCUMENTS

| | | |
|---|---|---|
| CN | 102387861 A | 3/2012 |
| CN | 102464539 A | 5/2012 |

(Continued)

OTHER PUBLICATIONS

Farcasiu, et al, "Preparation of sulfated zirconia catalysts with improved control over sulfur content," Applied Catalysis A: General 128 (1995) 97-105.*
Chinese Patent No. 102464539; Date of Publication: May 23, 2012; Abstract Only, 2 pages.
French Patent No. 2626572; Date of Publication: Aug. 4, 1989; Abstract Only, 1 page.

(Continued)

*Primary Examiner* — Fred M Teskin
(74) *Attorney, Agent, or Firm* — Cantor Colburn LLP

(57) ABSTRACT

A process for the preparation of a chemical composition comprising an aromatic compound a in a concentration B by weight, based on the total weight of the chemical composition, including: providing the following reaction components: a chemical composition comprising the following: the aromatic compound a in a concentration A by weight based on the total weight of the chemical composition, and an olefin in an amount of about 50 to about 99.99 wt. %, based on the total weight of the chemical composition, and an acidic solid; reacting the components to obtain the chemical composition comprising the aromatic compound a in a concentration B by weight based on the total weight of the chemical composition; wherein the concentration B is less than the concentration A.

19 Claims, 1 Drawing Sheet

(56) References Cited

U.S. PATENT DOCUMENTS

| | | | |
|---|---|---|---|
| 5,994,602 | A | 11/1999 | Abdul-Sada et al. |
| 6,028,024 | A | 2/2000 | Hirschauer et al. |
| 6,172,274 | B1 | 1/2001 | Gosling |
| 6,969,693 | B2 | 11/2005 | Sauvage et al. |
| 7,285,698 | B2 | 10/2007 | Liu et al. |
| 7,304,198 | B2 | 12/2007 | Wang et al. |
| 7,432,408 | B2 | 10/2008 | Timken et al. |
| 7,432,409 | B2 | 10/2008 | Elomari et al. |
| 7,476,774 | B2 | 1/2009 | Umansky et al. |
| 7,495,144 | B2 | 2/2009 | Elomari |
| 7,531,707 | B2 | 5/2009 | Harris et al. |
| 7,745,674 | B2 | 6/2010 | Boyer et al. |
| 7,732,651 | B2 | 8/2010 | Driver et al. |
| 7,842,738 | B2 * | 11/2010 | Milligan .............. B01J 19/2435 523/175 |
| 8,030,238 | B2 | 10/2011 | Spano et al. |
| 8,101,810 | B2 | 1/2012 | Boyer et al. |
| 8,124,821 | B2 | 2/2012 | Elomari et al. |
| 8,319,000 | B2 | 10/2012 | Hommeltoft |
| 2003/0060359 | A1 | 3/2003 | Olivier-Bourbigou et al. |
| 2005/0154243 | A1 | 7/2005 | Yeh et al. |
| 2006/0247479 | A1 | 11/2006 | Barchha et al. |
| 2007/0100184 | A1 | 5/2007 | Harmer et al. |
| 2007/0135656 | A1 | 6/2007 | Hobbs et al. |
| 2007/0142686 | A1 | 6/2007 | Campbell et al. |
| 2010/0160703 | A1 | 6/2010 | Driver et al. |
| 2010/0179359 | A1 | 7/2010 | Yeh et al. |
| 2011/0178355 | A1 | 7/2011 | Fritz et al. |
| 2011/0319693 | A1 | 12/2011 | Hommeltoft et al. |
| 2013/0150608 | A1 | 6/2013 | Winsett et al. |
| 2016/0347691 | A1 * | 12/2016 | Schmidt .............. C10G 29/205 |

FOREIGN PATENT DOCUMENTS

| | | |
|---|---|---|
| EP | 0404179 B1 | 12/1990 |
| EP | 2338955 A1 | 6/2011 |
| FR | 2626572 A1 | 8/1989 |
| FR | 2795403 A1 | 12/2000 |
| WO | 9420437 | 9/1994 |
| WO | 9850153 | 11/1998 |
| WO | 0041809 | 7/2000 |
| WO | 2012108861 A1 | 8/2012 |
| WO | 2013061336 A2 | 5/2013 |
| WO | 2015118470 A1 | 8/2015 |
| WO | 2015118471 A1 | 8/2015 |

OTHER PUBLICATIONS

French Patent No. 2795403; Date of Publication: Dec. 29, 2000; Abstract Only, 1 page.

International Search Report for International Application No. PCT/IB2015/050860; dated May 8, 2015; 5 pages.

Written Opinion of the International Search Report for International Application No. PCT/IB2015/050860; dated May 8, 2015; 5 pages.

Chinese Patent No. 102387861; Date of Publication: Mar. 21, 2012; Abstract Only, 1 page.

Hansmeier, A.R., "Ionic liquids as alternative solvents for aromatics extraction", University of Technology, 2010, 261 pages.

\* cited by examiner

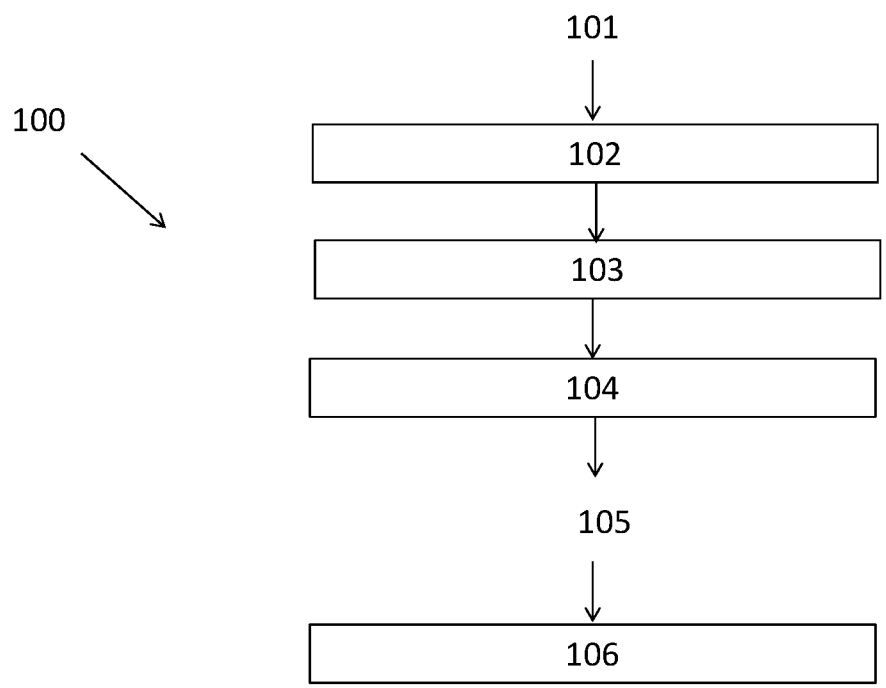

REMOVAL OF AROMATIC IMPURITIES FROM AN ALKENE STREAM USING AN ACID CATALYST

CROSS REFERENCE TO RELATED APPLICATIONS

This application is a 371 of International Application No. PCT/IB2015/050860, filed Feb. 5, 2015, which claims priority to U.S. Application No. 61/937,095, filed Feb. 7, 2014 both which are incorporated herein by reference in their entirety.

TECHNICAL FIELD

Disclosed herein is a process for the removal of aromatic impurities from an alkene stream using an acid catalyst. Also disclosed is a process for the preparation of downstream products preferably polymers and shaped bodies.

BACKGROUND

Alkenes, in particular α-olefins, have for a long time been desirable in the chemical industry. Due to the double bond, they can be converted into a number of other valuable compounds such as alcohols, aldehydes, ketones and organic halides, just to name a few. In polymerization reactions they can be used as monomer or co-monomer and are particularly valuable in the production of plastics. For reasons of toxicity, environmental safety and production efficiency, it is desirable to produce an alkene stream with reduced content of certain aromatic compounds, in particular benzene. Reduction of content of certain aromatic compounds is also a concern in terms of compliance with various governmental environmental regulation. There remains a need in the prior art for methods for the reduction of the content of certain aromatic compounds, particularly benzene, in alkene streams.

SUMMARY

Disclosed, in various embodiments, are processes for the preparation of a chemical composition comprising an aromatic compound.

A process for the preparation of a chemical composition comprising an aromatic compound α in a concentration B by weight, based on the total weight of the chemical composition, includes: a. providing the following reaction components: i. a chemical composition comprising the following: a) the aromatic compound α in a concentration A by weight based on the total weight of the chemical composition, and b) an olefin in an amount in of about 50 to about 99.99 wt. %, based on the total weight of the chemical composition, and ii. an acidic solid; and b. reacting the components to obtain the chemical composition comprising the aromatic compound α in a concentration B by weight based on the total weight of the chemical composition; wherein the concentration B is less than the concentration A.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

FIG. 1 is a schematic process flow diagram for the reduction in the content of certain aromatic compounds.

DETAILED DESCRIPTION

The present application is generally based on overcoming at least one of the problems encountered in the state of the art in relation to the reduction in the content of certain aromatic compounds in an alkene stream, in particular the reduction of benzene content in an alkene stream, particular where the alkene is an alpha olefin. This applies in particular to low concentrations of the aromatic compound, which should be removed in an industrial scale process.

Another problem is to provide an efficient and sustainable alkene source for producing downstream products and shaped bodies.

A contribution to solving at least one of the problems identified herein is made by a process for the preparation of a chemical composition comprising an aromatic compound α in a concentration B by weight, based on the total weight of the chemical composition, comprising:
  a. providing the following reaction components:
    i. a chemical composition comprising the following:
      a) The aromatic compound α in a concentration A by weight based on the total weight of the chemical composition,
      b) An olefin in an amount of about 50 to about 99.99 wt. %, preferably about 80 to about 99.99 wt. %, more preferably about 95 to about 99.99 wt. %, most preferably about 99 to about 99.99 wt. %, based on the total weight of the chemical composition,
    ii. an acidic solid;
  b. reacting the components to obtain the chemical composition comprising the aromatic compound α in a concentration B by weight based on the total weight of the chemical composition;
  wherein the concentration B is less than the concentration A.

In one embodiment of the process, the olefin b) is an α-olefin.

In one embodiment of the process, the olefin b) is a $C_2$-$C_{20}$ olefin, preferably a $C_2$-$C_{15}$ olefin, more preferably a $C_4$-$C_{10}$ olefin.

In one embodiment of the process, the olefin b) is a $C_6$-$C_{20}$ olefin, preferably a $C_6$-$C_{15}$ olefin, more preferably a $C_6$-$C_{10}$ olefin.

In one embodiment of the process, the concentration A is about 2 parts per million (ppm) to about 10 weight percent (wt. %), preferably about 3 ppm to about 5 wt. %, more preferably about 4 ppm to about 1 wt. %, based on the total weight of the chemical composition i.

In one embodiment of the process, the ratio of A:B is about 1:0 to about 1:0.1, preferably about 1:0 to about 1:0.01, more preferably about 1:0.1 to about 1:001.

In one embodiment of the process, the aromatic compound is benzene.

In one embodiment of the process, a further olefin is present as a component of a), wherein the further olefin is different to the olefin b).

In one embodiment of the process, the further olefin is a $C_2$-$C_{20}$ olefin, preferably a $C_2$-$C_{15}$ olefin, more preferably a $C_4$-$C_{10}$ olefin.

In one embodiment of the process, the acidic solid is one or more is selected from the following group:
a. a zeolite,
b. a sulphated zirconia,
c. an ion exchange resin,
d. a porous solid impregnated with an acid.

In one embodiment of the process, the acidic solid is a zeolite.

In one aspect of this embodiment, the zeolite is selected from analcime, chabazite, clinoptilolite, heulandite, natrolite, phillipsite, or stilbite, mordenite, Zeolite beta, ZSM-5, preferably natrolite, or a combination comprising at least one of the foregoing.

In one embodiment of the process, the acidic solid is a sulphated zirconia.

In one aspect of this embodiment, the sulphated zirconia has a content of sulphate groups of about 1 to about 10 moles per kilogram (mol/kg), preferably about 2 to about 8 mol/kg, more preferably about 3 to about 7 mol/kg.

In one embodiment of the process, the acidic solid is an ion exchange resin.

In one aspect of this embodiment, the ion exchange resin is a polystyrene sulphate or a derivative thereof.

In one embodiment of the process, the acidic solid is a porous solid impregnated with an acid.

In one aspect of this embodiment, the porous solid is one or more selected from zeolite, zirconia, sulphated zirconia, ion exchange resin, silica, or a combination comprising at least one of the foregoing.

In one aspect of this embodiment, the acid comprises a Lewis acid.

In one aspect of this embodiment, the Lewis acid has the general formula

wherein:
X is a halogen,
R is an alkyl group or hydrogen,
a is 1 or 2,
b in an of 0 to 3*a,
c is an integer equal to 3*a−b, and
M can be Al or B.

In one aspect of this embodiment, the acid comprises one or more selected from an acidic ionic liquid acid, a protic compound, a Bronsted acid, or a combination comprising at least one of the foregoing.

In one aspect of this embodiment, the acid comprises one or more selected from an ammonium, an imidazolium moiety, or a combination comprising at least one of the foregoing.

In one embodiment of the process, the acid is present in step b. in a concentration of about 0.1 to about 50 wt. %, preferably about 0.5 to about 20 wt. %, more preferably about 1 to about 5 wt. %, based on the total weight of the reaction components.

In one embodiment of the process, the acid is present in step b. in a concentration of about 1 to about 20 wt. %, preferably about 2 to about 10 wt. %, more preferably about 3 to about 5 wt. %.

In one embodiment of the process, the chemical composition i. is a homogeneous liquid.

In one embodiment of the process, the reaction b. is carried out at a temperature of about 0 to about 250° C., preferably about 30 to about 200° C., more preferably about 80 to about 150° C.

A contribution to solving at least one of the problems identified herein is made by a process for the preparation of a downstream product comprising the following steps:
i. preparation of an alkene by a process as described herein; and
ii. reaction of the alkene to form the downstream product.

In one embodiment of the process for the preparation of a downstream product, the downstream product is a polymer.

In one embodiment of the process for the preparation of a downstream product, the downstream product is a polyethene or a polypropene (e.g., polyethylene or polypropylene).

In one embodiment of the process for the preparation of a downstream product, the downstream product is converted into a shaped body.

A contribution to solving at least one of the problems identified herein is made by a process for the treatment of an olefin stream, preferably an α-olefin stream, in order to reduce the content of a certain aromatic compound α, preferably benzene.

In one embodiment, the content of the aromatic compound α is reduced by means of an alkylation reaction to yield an alkylated aromatic compound distinct from the aromatic compound α. In one aspect of this embodiment, the alkylated aromatic compound can differ from the aromatic compound α by a single additional alkylation or multiple additional alkylations. The alkylated aromatic compound preferably differs from the aromatic compound α by one, two or three additional alkylations. In one aspect of this embodiment, the product composition comprises at least two or more distinct alkylated aromatic compounds which can be distinct by virtue of a different number of alkyl groups, or different type of alkyl groups, or by a combination of both.

In another aspect, at least 50 wt. %, preferably at least 90 wt. %, more preferably at least 99 wt. % of the alkylated aromatic product is composed of a single alkylation product.

In one embodiment, the reaction of the aromatic compound, preferably the alkylation reaction, is catalyzed by an acid. In one aspect of this embodiment, a further catalyst, different from the acid catalyst, can be present.

The skilled person can choose the reaction conditions in any way he sees fit in order to increase the advantageous properties of the reaction.

It is preferred that the reaction be carried out in the liquid phase, preferably in a single homogeneous liquid phase.

It is preferred for the reaction to be carried out at a temperature of about 0 to about 250° C., preferably about 0 to about 200° C., more preferably about 0 to about 150° C.

It is preferred that the reaction be carried out at a pressure which allows a liquid phase reaction. In one embodiment, the reaction is carried out at a pressure of about 0.05 MegaPascals (MPa) to about 12 MPa (about 0.5 to about 120 bar), preferably about 0.05 MPa to about 6 MPa (about 0.5 to about 60 bar), more preferably about 0.05 MPa to about 2 MPa (about 0.5 to about 20 bar).

A contribution to solving at least one of the problems disclosed herein is made by a process for the treatment of a chemical composition comprising the following:
a) The aromatic compound α in a concentration A by weight based on the total weight of the chemical composition,
b) An olefin in an amount of about 50 to about 99.99 wt. %, preferably about 80 to about 99.99 wt. %, more preferably about 95 to about 99.999 wt. %, most preferably about 99 to about 99.9999 wt. %, based on the total weight of the chemical composition.

The olefin can be chosen according to the particular application. Preferred olefins are α-olefins and/or olefins which are employed as monomers and/or co-monomers in polymerization reactions. Preferred α-olefins in this context are those comprising carbon atoms of about 2 to about 30, preferably about 2 to about 15, more preferably about 2 to about 8. Preferred α-olefins are ethene, propene, but-1-ene, pent-1-ene, hex-1-ene, hept-1-ene, oct-1-ene, non-1-ene, dec-1-ene and higher α-olefins. The preferred α-olefins are hex-1-ene, hept-1-ene oroct-1-ene.

The alkene stream can contain a single olefin or can comprise at least two or more distinct olefins. In one embodiment, at least 50 wt. %, more preferably at least 90 wt. %, most preferably at least about 99 wt. % of the chemical composition i) is a single alkene. In another embodiment, the chemical composition comprises at least 10 wt. %, preferably at least 15 wt. %, more preferably at least 20 wt. % of a first olefin and at least 10 wt. %, preferably at least 15 wt. %, more preferably at least 20 wt. % of a second olefin distinct from the first olefin.

In a further embodiment, the alkene stream contains more than distinct alkenes, preferably with at least one of those alkenes being a $C_6$-$C_{20}$ alkene, preferably a $C_6$-$C_{15}$ alkene, more preferably a $C_6$-$C_{10}$ alkene. In one aspect of this embodiment, the alkene stream comprises hex-1-ene, preferably in an amount of about 50 to about 99 wt. %, more preferably about 65 to about 95 wt. %, most preferably about 75 to about 90 wt. %, based on the total weight of the alkene stream. In one aspect of this embodiment, the alkene stream comprises hept-1-ene, preferably in an amount of about 1 to about 30 wt. %, more preferably about 3 to about 20 wt. %, most preferably about 8 to about 15 wt. %, based on the total weight of the alkene stream. In one aspect of this embodiment, the alkene stream comprises oct-1-ene, preferably in an amount of about 0.1 to about 10 wt. %, more preferably about 0.5 to about 7 wt. %, most preferably about 1 to about 5 wt. %, based on the total weight of the alkene stream. In one aspect of this embodiment, the alkene stream comprises an alkene with more than 8 carbon atoms, preferably in an amount of about 0.1 to about 10 wt. %, more preferably about 0.5 to about 7 wt. %, most preferably about 1 to about 5 wt. %, based on the total weight of the alkene stream. In one aspect of this embodiment, the aromatic compound α, which is preferably benzene, is present in the alkene stream in a concentration A in an amount of about 2 ppm to about 1000 ppm, preferably about 20 ppm to about 700 ppm, more preferably about 100 ppm to about 400 ppm. In one aspect of this embodiment, the aromatic compound is present in the product stream in a concentration B in an amount of about 0 ppm to about 1 ppm, preferably about 0.01 ppm to about 0.5 ppm, more preferably 0.1 ppm to about 0.4 ppm.

The aromatic compound α can be chosen according to the particular application. Preferred aromatic compounds a are based on a benzene ring or on a naphthalene ring, preferably based on a benzene ring. The aromatic compound α can itself be singly alkylated multiply alkylated or not alkylated. The aromatic compound α is preferably not alkylated. Preferred aromatic compounds a are benzene, toluene, xylene, styrene, or a derivative of any of the preceding, or a mixture of at least two or more of the preceding, preferably benzene. Preferred substituents of the aromatic compound α are halogen, preferably F, Cl, Br or I, preferably F or Cl. Preferred isomers of xylene in this context are ortho, meta or para, or a combination of at least two or more thereof. The preferred aromatic compound α is benzene.

In one embodiment, the aromatic content of the composition i) consists of at least 50 wt. %, preferably at least 90 wt. %, more preferably at least about 99 wt. % of a single aromatic compound, based on the total weight of aromatic compounds in the composition i). In another embodiment, the aromatic content of the composition i) comprises at least 10 wt. %, preferably at least 15 wt. %, more preferably at least 20 wt. % of a first aromatic compound and at least about 10 wt. %, preferably at least about 15 wt. %, more preferably at least about 20 wt. % of a second aromatic compound, in each case based on the total weight of aromatic compounds in the composition i).

The acidic solid ii. preferably catalyzes the reaction which reduces the content of aromatic compound α in the composition i). The skilled person has knowledge of acidic solids and their use as chemical catalysts. He can select any acidic which he considers fit for improving the advantageous characteristics of the reaction.

The acidic solid particles preferably have diameters of about 50 picometers (pm) to about 10 millimeters (mm), preferably about 60 pm to about 5 mm, more preferably about 80 pm to about 4 mm.

Preferred acidic solids are one or more selected from the following:
I. a zeolite;
II. a sulphated zirconia;
III. an ion exchange resin;
IV. a porous solid impregnated with an acid Natural or synthetic zeolites can be employed, synthetic zeolites being preferred. The zeolite can contain one or more than one zeolite and/or other non-zeolite constituents. It is preferred for the zeolite to have a low non-zeolite content, preferable less than about 5 wt. %, more preferably less than about 1 wt. %, most preferably less than about 0.1 wt. %. In one embodiment, the zeolite comprises at least about 90 wt. %, preferably at least about 95 wt. %, most preferably at least about 99 wt. % of a single zeolite. In another embodiment, the zeolite comprises at least about 10 wt. %, preferably at least about 30 wt. %, most preferably at least about 40 wt. % of a first zeolite and at least about 10 wt. %, preferably at least about 30 wt. %, most preferably at least about 40 wt. % of a second zeolite, distinct from the first zeolite.

The skilled person has knowledge of zeolites and he can select any zeolite which he considers suitable for improving the advantageous properties of the process. Preferred zeolites are the following: analcime, chabazite, clinoptilolite, heulandite, natrolite, phillipsite, mordenite, ZSM-5, zeolite-beta or stilbite, preferably ZSM-5.

Preferred cations contained in the zeolite are one or two or more selected from the following: $Na^+$, $K^+$, $Ca^{2+}$, $Mg^{2+}$, or a combination comprising at least one of the foregoing, preferably $Na^+$.

Preferred zeolites comprise Bronsted and or Lewis acid sites. In one embodiment, the zeolite comprises more Bronsted acid sites than Lewis acid sites. In another embodiment, the zeolite comprises more Lewis acid sites than Bronsted acid sites.

The zeolite and the cation can be selected by the skilled person in order to provide the required level of acidity and/or otherwise improve the advantageous properties of the process. More information on the properties and syntheses of zeolites can be found in "Handbook of Zeolite Science and Technology"—Auerbach, Carrado & Dutta, 2003, Marcel Dekker publishers.

The skilled person has knowledge of sulphated zirconias and he can select the sulphated zirconia in order to provide the required level of acidity and/or otherwise improve the advantageous properties of the process.

The sulphated zirconia is preferably prepared by drying and/or calcinating hydrous or anhydrous zirconium sulphate. Drying and/or calcination is preferably carried out at a temperature of about 100 to about 800° C., more preferably about 200 to about 600° C., most preferably about 300 to about 600° C. It is preferred for the sulphated zirconia to be prepared according by a method disclosed in the following: "Structural and Acidity Studies of Sulphated Zirconia Prepared from Zirconium Sulphate"—Didik Prasetyoko, Zainab Ramli, Salasiah Endud and Hadi Nu—Majalah IPTEK—Vol. 17, No. 2, Mei 2006, which is hereby incorporated into this application in its entirety.

The sulphated zirconia preferably has a content of sulphate groups of about 1 to about 10 mol/kg, preferably about 2 to about 8 mol/kg, more preferably about 3 to about 7 mol/kg.

Preferred sulphated zirconias comprise Bronsted and or Lewis acid sites. In one embodiment, the sulphated zirconia comprises more Bronsted acid sites than Lewis acid sites. In another embodiment, the sulphated zirconia comprises more Lewis acid sites than Bronsted acid sites.

The skilled person has knowledge of ion exchange resins and he can choose an ion exchange resin which he considers appropriate for bringing about the desired acidity and or other advantageous properties of the process.

Preferred ion exchange resins in this context are solid polymer substrates, preferably porous, preferably in the form of beads. Preferred ion exchange resins are based on a polystyrene, which preferably comprises functional groups, preferably polystyrene sulphate, the polystyrene preferably being cross-linked. Preferred functional groups in the ion exchange resin are at least one or more selected from sulphonic acid, sulphonate, amino groups, carboxylic acid, or a combination comprising at least one of the foregoing, preferably sulphonic acid. Preferred cations in the ion exchange resin are $Na^+$, $K^+$, $Li^+$, $H^+$, $H30^+$, preferably $H^+$ or $Na^+$.

Preferred porous solids impregnated with acid are based on one or more of the following porous solids: a zeolite, a zirconia, a sulphated zirconia, an ion exchange resin, a silica; preferably a zeolite. The porous solid can be microporous, preferably with a pore size less than about 2 nanometers (nm). In some cases, microporous solids have a pore size as small as 0.01 nm or more. The porous solid can be mesoporous, preferably with a pore size of about 2 nm to less than about 50 nm. The porous solid can be macroporous, preferably with a pore size of at least about 50 nm, or a pore size of at least about 75 nm. In some cases, macroporous solids have a pore size as large as up to about 1 pm or less.

Preferred porous solids impregnated with acid are preferably impregnated with a Lewis acid and or a Bronsted acid.

Preferred Lewis acids in this context are compounds which are capable of accepting at least one or more than one lone pair. The skilled person has knowledge of Lewis acids and can select the Lewis acid in any way he sees fit in order to enhance the advantageous properties of the reaction.

Preferred Lewis acids comprise at least one or two or more Lewis acid centers or atoms which are capable of accepting at least one or two or more lone pairs. In one embodiment, the Lewis acid comprises at least one or two or more selected from the list consisting of the following: B, Al, P, As, Sb, Si, Ge, Se, Te, I, Be, S, or a combination comprising at least one of the foregoing; preferably selected from the list consisting of the following: B, Al, P, As, Sb or Si, or a combination comprising at least one of the foregoing; more preferable selected from the list consisting of the following: B, Al, or a combination comprising at least one of the foregoing. The most preferred Lewis acids comprise at least one or two or more Al atoms.

Preferred Lewis acids comprising Al are of the general formula

$Al_nY_{3n}$ wherein:
n is an integer in of about 1 to about 10, preferably about 1 to about 5, preferably 1 or 2, most preferably 1;
Y is a hydrocarbon residue, preferably an alkyl group, a halogen, an alkoxy group, a thioalkyl group, or hydrogen, wherein the Y within a single molecule can be the same as or different to each other. Y is preferably alkyl, H or halogen.

In one embodiment, the Lewis acid has the general formula

$Al_aX_bR_c$, wherein:
X is a halogen, preferably F, Br, or Cl, more preferably Cl;
R is an alkyl group, preferably a $C_1$-$C_{10}$ alkyl, more preferably a $C_1$-$C_5$ alkyl, most preferably ethyl;
m is 1 or 2;
b is an integer of 0 to 3*a; and
c is in integer of 0 to 3*a–b.

In one embodiment, preferred Lewis acids are at least one or two or more selected from the list consisting of the following: $AlCl_3$, $AlBr_3$, $AlH_3$, $AlF_3$, $Al(alkyl)_3$, preferably $AlEth_3$, $BH_3$, $BF_3$, $BCl_3$, or a combination comprising at least one of the foregoing.

In another embodiment, the Lewis acid is of the form general form $Al_2Cl_nEth_{6-n}$, wherein n is an integer of about 2 to about 6. In one aspect of this embodiment, the Lewis acid is $Al_2Cl_3Eth_3$.

Preferred Bronsted acids in this context are compounds which are capable of donating at least one or more than one proton. The skilled person has knowledge of Bronsted acids and can select the Bronsted acid in any way he sees fit in order to enhance the advantageous properties of the reaction.

In one aspect of this embodiment, the Bronsted acid comprises at least one or more than one N—H bond, preferably present in a positive ion. In this context it is preferred that the Bronsted acid comprise at least one or more than one cation selected from ammonium or derivative thereof, imidazolium or derivative thereof, pyrazolium or derivative thereof, oxazolium or derivative thereof, pyridinium or derivative thereof, isoxazolium or derivative thereof, thiazolium or derivative thereof, preferably ammonium or derivative thereof or imidazolium or derivative thereof, or a combination comprising at least one of the foregoing.

In one embodiment, the Bronsted acid is cyclic, preferably comprising at least one N atom and preferably at least one N—H bond.

In one embodiment of the process, the Bronsted acid comprises at least one ammonium.

In one aspect of this embodiment, the ammonium has the general formula $NR_4^+$, wherein R is hydrocarbon or hydrogen, and wherein each R can be the same as or different to the other R in the molecule. In further aspects of this embodiment, the ammonium can be primary, secondary or tertiary ammonium. Preferred hydrocarbons R are alkyl or aromatic, preferably alkyl. Alkyl groups R can be n-alkyl, iso-alkyl, tert-alkyl, preferably n-alkyl. Preferred alkyl groups R are methyl, ethyl, propyl butyl, pentyl or hexyl, preferably methyl or ethyl, more preferably ethyl.

In one embodiment of the process, the Bronsted acid comprises an imidazolium.

In one aspect of this embodiment, the imidazolium has the general formula

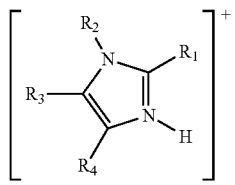

wherein $R_2$ is alkyl, preferably methyl or butyl, more preferably butyl;

wherein each of $R_1$, $R_3$, $R_4$ is hydrocarbon, preferably alkyl, or hydrogen;

wherein $R_1$, $R_2$, $R_3$, $R_4$ within a molecule can be the same as or different to each other.

In one embodiment, the imidazolium is singly substituted, $R_2$ is alkyl, preferably methyl or butyl, more preferably butyl, $R_1$, $R_3$ and $R_4$ are each hydrogen.

In one embodiment, the imidazolium is doubly substituted. $R_2$ is alkyl, preferably methyl or butyl, more preferably butyl. In one aspect of this embodiment, $R_1$ is a hydrocarbon, preferably alkyl, more preferably methyl or butyl, most preferably methyl; and $R_3$ and $R_4$ are hydrogen. In one aspect of this embodiment, $R_3$ is a hydrocarbon, preferably alkyl, more preferably methyl or butyl, most preferably methyl; and $R_4$ are hydrogen. In one aspect of this embodiment, $R_4$ is a hydrocarbon, preferably alkyl, more preferably methyl or butyl, most preferably methyl; and $R_3$ and $R_1$ are hydrogen.

In one embodiment, the imidazolium is triply substituted. $R_2$ is alkyl, preferably methyl or butyl, more preferably butyl. In one aspect of this embodiment, $R_1$ and $R_3$ are hydrocarbon, preferably alkyl, more preferably methyl or butyl, most preferably methyl, and $R_1$ and $R_3$ can be the same as or different to each other; and $R_4$ is hydrogen. In one aspect of this embodiment, $R_1$ and $R_4$ are hydrocarbon, preferably alkyl, more preferably methyl or butyl, most preferably methyl, and $R_1$ and $R_4$ can be the same as or different to each other; and $R_3$ is hydrogen. In one aspect of this embodiment, $R_4$ and $R_3$ are hydrocarbon, preferably alkyl, more preferably methyl or butyl, most preferably methyl, and $R_4$ and $R_3$ can be the same as or different to each other; and $R_1$ is hydrogen.

In one embodiment, the imidazolium is four times substituted. $R_2$ is alkyl, preferably methyl or butyl, more preferably butyl. $R_1$, $R_3$, and $R_4$ are each hydrocarbon, preferably alkyl, more preferably methyl or butyl, most preferably methyl. $R_1$, $R_2$, $R_3$, and $R_4$ can be the same as or different to each other in the molecule.

Preferred imidazoliums are alkyl substituted imidazolium, wherein the alkyl groups are preferably one or more than one selected from the following: methyl, ethyl, propyl, butyl, pentyl, hexyl, preferably methyl or butyl, or a combination comprising at least one of the foregoing. The imidazolium is preferably substituted at one or more than one of the following position: 1 ($R_2$), 2 ($R_1$), 4 ($R_4$), 5 ($R_3$), preferably 1 ($R_2$) and/or 4 ($R_4$). Preferred imidazolium derivatives are dimethyl imidazolium, preferably 1,4-dimethyl imidazolium; di butyl imidazolium, preferably 1,4-dibutyl imidazolium; methyl imidazolium, preferably 1-methyl imidazolium; butyl imidazolium, preferably 1-butyl imidazolium; methyl-butyl imidazolium, preferably 1-methyl-4-butyl-imidazolium or 1-butyl-4-methyl imidazolium.

In one embodiment of the process, the Bronsted acid comprises an anion selected from $AlCl_4^-$, $Cl^-$, $Br^-$, $I^-$, or a combination comprising at least one of the foregoing, preferably $AlCl_4^-$.

In one embodiment, acid comprises 1-butyl imidazolium aluminum tetra chloride.

In one embodiment of the process for the preparation of chemical composition, preferably an olefin stream, with a reduced content of a certain aromatic compound, preferably a reduced benzene content, is coupled to further subsequent reactions in order to obtain downstream products. Preferred downstream products are those obtained from polymerization reactions, hydrogenation reactions, halogenation reactions, and other chemical functionalization reactions, preferably polymerization reactions. Preferred monomeric downstream products are vinyl chloride monomer (VCM), ethylene glycol monomer (MEG), ethylene oxide (EO), acrylonitrile, butadiene, styrene, vinyl acetate monomer (VAM). Preferred oligomers are olefins, preferably linear olefins, preferably alpha olefins, preferably linear alpha olefins, such as 1-butene, 1-hexene, 1-octene, 1-decene, 1-dodecene, 1-tetradecene, 1-hexadecene or 1-octadecene. Preferred polymerization reactions can be mono-polymerization reactions or co-polymerization reactions. Preferred polymerization products are polythenes, substituted polythenes, polythene derivatives, polyvinyl chlorides, polyethylene glycols (PEG), acrylonitrile butadiene styrenes (ABS), polyvinyl acetates, poly olefins, preferably poly alpha olefins (PAO), styrene butadiene rubber (SBR), and other polymers comprising at least one of the above described monomers. Preferred polymers are polythenes or polythene derivatives. Preferred forms of polythene and its derivatives are ultra-high-molecular-weight polyethylene (UHMWPE), ultra-low-molecular-weight polyethylene (ULMWPE or PE-WAX), high-molecular-weight polyethylene (HMWPE), high-density polyethylene (HDPE), high-density cross-linked polyethylene (HDXLPE), cross-linked polyethylene (PEX or XLPE), medium-density polyethylene (MDPE), linear low-density polyethylene (LLDPE), low-density polyethylene (LDPE), or very-low-density polyethylene (VLDPE), chlorinated polyethylene (CPE), or combinations of at least two thereof, preferably HDPE, LLDPE or LDPE. Preferred functionalization products are aromatic or non-aromatic compounds, saturated or unsaturated compounds, ketones, aldehydes, esters, amides, amines, carboxylic acids, alcohols etc.

In one embodiment, the downstream products are further processed, particularly in the case where the downstream product is a polymer, particularly when it is polythene or a derivative thereof. In one embodiment, this further processing preferably involves formation of shaped objects such as plastic parts for electronic devices, automobile parts, such as bumpers, dashboards, or other body parts, furniture, or other parts or merchandise, or for packaging, such as plastic bags, film, or containers.

FIG. 1 shows a schematic process flow diagram 100 for the reduction in the content of certain aromatic compound α, preferably benzene, of a chemical composition, preferably an olefin stream, preferably an α-olefin stream, wherein the chemical composition enters the process with a content A of the aromatic compound 101 and exits the process with a content B of the aromatic compound α 105. The chemical composition 101 can first optionally undergo pre-processing 102, preferably one or more selected from: heating, cooling, filtration, distillation, or a combination comprising at least one of the foregoing. The chemical corn-composition is then contacted with the acid 103, preferably comprising a protic compound, preferably comprising an ammonium and/or an imidazolium. The chemical composition is then optionally post-processed 104, preferably one or more selected from the following: heating, cooling, filtration, distillation, or a combination comprising at least one of the foregoing. Following the process to reduce the content of the aromatic compound α, the chemical composition 105 can optionally be used as a reactant in a further downstream reaction 106, preferably a polymerization reaction, to produce a downstream product, preferably a poly α-olefin.

The content of aromatic compound α was determined using Capillary gas chromatography. Where the aromatic compound α was benzene, The ASTM international standard method ASTM D6229-06 (2010) was used.

The following examples are merely illustrative of the process disclosed herein and are not intended to limit the scope hereof.

EXAMPLES

Example 1

100 milliliters (ml) of a hydrocarbon mixture with the composition given in column 2 of Table 1 was reacted (heat treated under inert conditions in a nitrogen stream) with 5 grams (g) H-ZSM-5 in a batch reactor (Parr 300 ml Autoclave Model 4566 Mini Benchtop reactor). The reaction was carried out at 0.1 MPa (1 bar), 120° C. for 30 minutes under stirring. The hydrocarbon mixture following reaction is given in column 3 of Table 1.

The above example was repeated with 5 g H-Mordenite and repeated with 5 g Zeolite-Beta in place of 5 g H-ZSM-5. These zeolites are commercially available from Sigma-Aldrich. In both cases a significant reduction of benzene content was observed.

Example 2

Example 1 was repeated except with 5 g sulphated zirconia in place of 5 g H-ZSM-5. For this purpose, calcined zirconium dioxide (at 550° C.) for 2 hours was washed with sulphuric acid, dried at 110° C. for 2 hours and calcined again at 425° C. for 2 hours. The obtained compound was carefully crushed and sieved to remove fine powder of diameter less than 100 pm. 5 g of the obtained course particles not exceeding 2 mm in diameter were used for the reaction with the hydrocarbon mixture. The composition of the hydrocarbon mixture following reaction is given in column 4 of Table 1.

Example 3

Example 1 was repeated except with 5 g ion exchange resin—polystyrene sulfonate (also obtained from Sigma-Aldrich)—in place of the 5 g zeolite. The hydrocarbon mixture following reaction is given in column 5 of Table 1.

Example 4

Example 1 was repeated except with 5 g porous clay impregnated with sulphuric acid, dried at 110° C. for 2 hours and calcined at 425° C. for 2 hour in place of the 5 g zeolite. The hydrocarbon mixture following reaction is given in column 6 of Table 1.

TABLE 1

| Hydrocarbon Component | Reactant Mixture | Product Mixture Example 1 | Product Mixture Example 2 | Product Mixture Example 3 | Product Mixture Example 4 |
| --- | --- | --- | --- | --- | --- |
| Hex-1-ene | 82 wt. % | 82 wt. % | 82 wt. % | 82 wt. % | 82 wt. % |
| Hept-1-ene | 13 wt. % | 13 wt. % | 13 wt. % | 13 wt. % | 13 wt. % |
| Octo-1-ene | 2.5 wt. % | 2.5 wt. % | 2.5 wt. % | 2.5 wt. % | 2.5 wt. % |
| Alkenes with more than 8 carbon atoms | 2.5 wt. % | 2.5 wt. % | 2.5 wt. % | 2.5 wt. % | 2.5 wt. % |
| Benzene | 251.3 ppm | 10.9 ppm | 9.7 ppm | 17.7 ppm | 20.1 ppm |

The process disclosed herein includes at least the following embodiments:

Embodiment 1

A process for the preparation of a chemical composition comprising an aromatic compound α in a concentration B by weight, based on the total weight of the chemical composition, comprising: a. providing the following reaction components: i. a chemical composition comprising the following: a) the aromatic compound α in a concentration A by weight based on the total weight of the chemical composition, and b) an olefin in an amount in of about 50 to about 99.99 wt. %, based on the total weight of the chemical composition, and ii. an acidic solid; and b. reacting the components to obtain the chemical composition comprising the aromatic compound α in a concentration B by weight based on the total weight of the chemical composition; wherein the concentration B is less than the concentration A.

Embodiment 2

The process according to Embodiment 1, wherein the olefin b) is an α-olefin.

Embodiment 3

The process according to any of the preceding embodiments, wherein the olefin b) is a $C_2$-$C_{20}$ olefin.

Embodiment 4

The process according to any of the preceding embodiments, wherein the concentration A is in an amount of about 2 ppm to about 10 wt. % based on the total weight of the chemical composition i.

Embodiment 5

The process according to any of the preceding embodiments, wherein the ratio of concentration A:concentration B is about 1:0 to about 1:0.1.

Embodiment 6

The process according to any of the preceding embodiments, wherein the aromatic compound is benzene.

Embodiment 7

The process according to any of the preceding embodiments, wherein a further olefin is present as a component of a), wherein the further olefin is different to the olefin b).

Embodiment 8

The process according to Embodiment 7, wherein the further olefin is a $C_2$-$C_{20}$ olefin.

Embodiment 9

The process according to any of the preceding embodiments, wherein the acidic solid is selected from a zeolite, a sulphated zirconia, an ion exchange resin, a porous solid impregnated with an acid, or a combination comprising at least one of the foregoing.

Embodiment 10

The process according to any of the preceding embodiments, wherein the acidic solid is a zeolite.

Embodiment 11

The process according to Embodiment 10, wherein the zeolite is selected from analcime, chabazite, clinoptilolite, heulandite, natrolite, phillipsite, stilbite, or a combination comprising at least one of the foregoing.

Embodiment 12

The process according to any of Embodiments 1 to 9, wherein the acidic solid is a sulphated zirconia.

Embodiment 13

The process according to Embodiment 12, wherein the sulphated zirconia has a content of sulphate groups of about 1 mol/kg to about 10 mol/kg.

Embodiment 14

The process according to any of Embodiments 1 to 9, wherein the acidic solid is an ion exchange resin.

Embodiment 15

The process according to Embodiment 14, wherein the ion exchange resin is a polystyrene sulphate or a derivative thereof.

Embodiment 16

The process according to any of Embodiments 1 to 9, wherein the acidic solid is a porous solid impregnated with an acid.

Embodiment 17

The process according to Embodiment 16, wherein the porous solid is selected from wing: zeolite, zirconia, sulphated zirconia, ion exchange resin, silica, or a combination comprising at least one of the foregoing.

Embodiment 18

The process according to Embodiment 16 or 17, wherein the acid comprises a Lewis acid.

Embodiment 19

The process according to Embodiment 18, wherein the Lewis acid has the general formula $M_aX_bR_c$ wherein: X is a halogen, R is an alkyl group or hydrogen, a is 1 or 2, b is an integer of 0 to 3*a, c is an integer equal to a*3−b, and M is Al or B.

Embodiment 20

The process according to any of Embodiments 16 to 19, wherein the acid comprises an acidic ionic liquid, a protic compound, a Bronsted acid, or a combination comprising at least one of the foregoing.

Embodiment 21

The process according to any of Embodiments 16 to 20, wherein the acid comprises an ammonium, an imidazolium, or a combination comprising at least one of the foregoing.

Embodiment 22

The process according to any of the preceding embodiments, wherein the acidic solid is present in step b. in a concentration of about 0.1 to about 50 wt. %, based on the total weight of the reaction components.

Embodiment 23

The process according to any of the preceding embodiments, wherein the acid is present in step b. in a concentration of about 1 to about 20 wt. %, based on the total weight of the reaction components.

Embodiment 24

The process according to any of the preceding embodiments, wherein the reaction b. is carried out at a temperature of about 0 to about 250° C.

Embodiment 25

A process for the preparation of a downstream product comprising: i. preparation of an alkene by a process according to any of preceding embodiments; and ii. reaction of the alkene to form the downstream product.

Embodiment 26

The process according to Embodiment 25, wherein the downstream product is a polymer.

Embodiment 27

The process according to Embodiment 25 or 26, wherein the downstream product is a polythene or a polypropene.

Embodiment 28

The process according to any of Embodiments 25 to 27, wherein the downstream product is converted into a shaped body.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A process for the preparation of a chemical composition comprising an aromatic compound $\alpha$ in a concentration B by weight, based on the total weight of the chemical composition, comprising:
   a. providing the following reaction components:
      i. a chemical composition comprising the following:
         a) The aromatic compound $\alpha$ in a concentration A by weight based on the total weight of the chemical composition, and
         b) An olefin in an amount of about 50 to about 99.99 wt. %, based on the total weight of the chemical composition, wherein the olefin is a C4-C10 olefin, and
      ii. an acidic solid; and
   b. reacting the components to obtain the chemical composition comprising the aromatic compound $\alpha$ in a concentration B by weight based on the total weight of the chemical composition;
wherein the concentration B is less than the concentration A;
wherein there is a greater than 96% reduction of benzene impurities by weight in the chemical composition.

2. The process according to claim 1, wherein the olefin b) is an $\alpha$-olefin.

3. The process according to claim 1, wherein the concentration A is in an amount of about 2 ppm to about 10 wt. % based on the total weight of the chemical composition i.

4. The process according to claim 1, wherein the ratio of concentration A:concentration B is about 1:0 to about 1:0.1.

5. The process according to claim 1, wherein the aromatic compound $\alpha$ is benzene.

6. The process according to claim 1, wherein a further olefin is present as a component of a), wherein the further olefin is different to the olefin b).

7. The process according to claim 1, wherein the acidic solid is selected from a zeolite, a sulphated zirconia, an ion exchange resin, a porous solid impregnated with an acid, or a combination thereof.

8. The process according to claim 1, wherein the acidic solid is a zeolite selected from analcime, chabazite, clinoptilolite, heulandite, natrolite, phillipsite, stilbite, or a combination thereof.

9. The process according to claim 1, wherein the acidic solid is a sulphated zirconia, wherein the sulphated zirconia has a content of sulphate groups of about 1 mol/kg to about 10 mol/kg.

10. The process according to claim 1, wherein the acidic solid is an ion exchange resin.

11. The process according to claim 1, wherein the acidic solid is a porous solid impregnated with an acid.

12. The process according to claim 11, wherein the acid comprises a Lewis acid, wherein the Lewis acid has the general formula

wherein:
X is a halogen,
R is an alkyl group or hydrogen,
a is 1 or 2,
b is an integer of 0 to 3*a,
c is an integer equal to a*3−b, and
M is Al or B.

13. The process according to claim 11, wherein the acid comprises an acidic ionic liquid, a protic compound, a Bronsted acid, or a combination comprising at least one of the foregoing.

14. The process according to claim 1, wherein the acidic solid is present in step b. in a concentration of about 0.1 to about 50 wt. %, based on the total weight of the reaction components.

15. The process according to claim 1, wherein the acidic solid is present in step b. in a concentration of about 1 to about 20 wt. %, based on the total weight of the reaction components.

16. The process according to claim 1, wherein the reaction b. is carried out at a temperature of about 0 to about 250° C.

17. A process for the preparation of a downstream product comprising:
i. preparation of an alkene by a process according to claim 1; and
ii. reaction of the alkene to form the downstream product.

18. The process according to claim 17, wherein the downstream product is a polymer.

19. The process according to claim 17, wherein the downstream product is converted into a shaped body.

* * * * *